United States Patent
Manhart et al.

(10) Patent No.: US 12,361,540 B2
(45) Date of Patent: Jul. 15, 2025

(54) PROVISION OF CORRECTED MEDICAL IMAGE DATA

(71) Applicant: Siemens Healthcare GmbH, Erlangen (DE)

(72) Inventors: Michael Manhart, Fürth (DE); Alexander Preuhs, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 640 days.

(21) Appl. No.: 17/552,691

(22) Filed: Dec. 16, 2021

(65) Prior Publication Data
US 2022/0189013 A1  Jun. 16, 2022

(30) Foreign Application Priority Data
Dec. 16, 2020 (DE) .................. 10 2020 216 017.1

(51) Int. Cl.
*G06T 7/00* (2017.01)
*G06T 5/77* (2024.01)

(52) U.S. Cl.
CPC .............. *G06T 7/0012* (2013.01); *G06T 5/77* (2024.01); *G06T 2207/10081* (2013.01);
(Continued)

(58) Field of Classification Search
CPC ............ G06T 7/0012; G06T 5/77; G06T 2207/10081; G06T 2207/10104; G06T 2207/10116; G06T 2207/20081
See application file for complete search history.

(56) References Cited

U.S. PATENT DOCUMENTS

2006/0003328 A1\* 1/2006 Grossberg ........... G10L 21/0364
702/20
2013/0010920 A1  1/2013 Wein et al.
(Continued)

FOREIGN PATENT DOCUMENTS

DE  102020211032 A1  4/2021
EP  2546804 A1  1/2013

OTHER PUBLICATIONS

Herbst, Magdalena, et al. "Misalignment compensation for ultra-high-resolution and fast CBCT acquisitions." Medical Imaging 2019: Physics of Medical Imaging. vol. 10948. International Society for Optics and Photonics, 2019. pp. 1-8.
(Continued)

*Primary Examiner* — Kevin Ky
(74) *Attorney, Agent, or Firm* — Lempia Summerfield Katz LLC

(57) ABSTRACT

A method includes receiving image data of an examination object. A first temporary data record is created by applying a first correction to the image data. A further temporary data record is created by applying a further correction to the image data. The further correction at least partially corresponds to the first correction. A trained function is applied to input data that is based on the first temporary data record and the further temporary data record. A parameter of the trained function is based on an image quality metric. It is determined whether the first temporary data record has a higher image quality compared with the further temporary data record. When a result is positive, the first temporary data record is provided as the corrected medical image data. When the result is negative, the further temporary data record is provided as the image data, and part of the method is repeated.

15 Claims, 5 Drawing Sheets

(52) U.S. Cl.
CPC ............... *G06T 2207/10104* (2013.01); *G06T 2207/10116* (2013.01); *G06T 2207/20081* (2013.01)

(56) References Cited

U.S. PATENT DOCUMENTS

| | | | | |
|---|---|---|---|---|
| 2016/0358321 | A1* | 12/2016 | Xu ........................ | G06N 3/045 |
| 2019/0050973 | A1* | 2/2019 | Bernal .................. | H04N 23/80 |
| 2019/0354895 | A1* | 11/2019 | Vasudevan ............. | G06N 3/006 |
| 2020/0020097 | A1* | 1/2020 | Do ..................... | G06F 18/2413 |
| 2020/0286264 | A1 | 9/2020 | Kaethner | |
| 2020/0357118 | A1* | 11/2020 | Yao ........................ | G06N 3/045 |
| 2021/0343398 | A1* | 11/2021 | Bijalwan ................ | G06V 10/82 |
| 2022/0061816 | A1* | 3/2022 | Lee ...................... | A61B 8/5207 |
| 2022/0189013 | A1* | 6/2022 | Manhart ............... | G06T 7/0012 |
| 2024/0169543 | A1* | 5/2024 | Zhu .......................... | G06T 7/11 |

OTHER PUBLICATIONS

Preuhs, Alexander, et al. "Image quality assessment for rigid motion compensation." arXiv preprint arXiv:1910.04254 (2019). pp. 1-5.
Wikipedia "Machine Learning" https://de.wikipedia.org/w/index.phptitle=Maschinelles_Lernen&oldid=204714424 Retrieved Sep. 9, 2021. pp. 1-11 with English translation.
Wikipedia "Metaheuristic" https://de.wikipedia.org/w/index.phptitle=Metaheuristik&oldid=171260041Retrieved Sep. 7, 2021. pp. 1-14 with English translation.

* cited by examiner

PROVISION OF CORRECTED MEDICAL IMAGE DATA

This application claims the benefit of German Patent Application No. DE 10 2020 216 017.1, filed Dec. 16, 2020, which is hereby incorporated by reference in its entirety.

BACKGROUND

The present embodiments relate to a computer-implemented method for the provision of corrected medical image data, a computer-implemented method for the provision of a trained function, a provision unit, a medical imaging device, and a computer program product.

When mapping an examination region of an examination object using a medical imaging device, image artifacts may occur in the medical image data due to movement of the examination object and/or the imaging device and/or due to further interference sources such as metal objects, for example. For the purpose of retrospective correction of the image data, use is often made of image processing algorithms (e.g., for movement compensation). These image processing algorithms are often configured as high-dimensional optimization problems. This may have the disadvantageous consequence that the optimum obtained by applying the image processing algorithm represents only a local optimum, and, for example, not a global optimum. This may provide that the full potential of the image processing algorithms cannot be used for correction of the image data. The may also provide that interfering image artifacts may remain in the processed image data.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved correction of medical image data is enabled.

Methods and apparatuses for the provision of corrected medical image data and methods and apparatuses for the provision of a trained function are provided. In this context, features, advantages, and alternative embodiments of data structures and/or functions used in methods and apparatuses for the provision of corrected medical image data may be transferred to analogous data structures and/or functions used in methods and apparatuses for the provision of a trained function. Analogous data structures in this context may be identified, for example, by the use of the prefix "training". Further, the trained functions used in methods and apparatuses for the provision of corrected medical image data may be adjusted and/or provided, for example, by methods and apparatuses for the provision of a trained function.

In a first aspect, a computer-implemented method for the provision of corrected medical image data is provided. In a first act a), medical image data of an examination object is received. In a second act b), a first temporary data record is created by applying a first correction to the image data. In a third act c), at least one further temporary data record is created by applying a further correction to the image data. In this case, the further correction corresponds to the first correction with at least one interference term that is applied to at least one parameter of the first correction. In a fourth act d), a trained function is applied to input data. In this case, the input data is based on the first temporary data record and on the at least one further temporary data record. Further, at least one parameter of the trained function is based on an image quality metric. The application of the trained function to the input data determines whether the first temporary data record has a higher image quality compared with the at least one further temporary data record. If the result is positive, the first temporary data record is provided as the corrected medical image data. If the result is negative, the at least one further temporary data record is provided as the image data in act b). Further, in the latter case, the acts b) to d) are executed again.

The acts described above and forming part of the method for the provision of corrected medical image data may be executed simultaneously and/or consecutively at least to some extent.

The receipt of the medical image data in act a) may include, for example, capture and/or readout from a computer-readable data memory and/or receipt from a data memory unit (e.g., a database). Further, the medical image data may be provided by a provision unit of a medical imaging device. In this case, the medical image data may be recorded by the medical imaging device.

The examination object may be a human and/or animal patient. Further, the examination object may be an examination phantom.

The medical image data may include a two-dimensional (2D) and/or three-dimensional (3D) mapping of the examination object (e.g., the examination region). Further, the medical image data may map the examination object with temporal resolution. Further, the first image data records may include metadata, where the metadata may include, for example, information relating to a recording parameter and/or operating parameter of the medical imaging device.

For the purpose of creating the first temporary data record in act b), a first correction may be applied to the medical image data. In this case, the first temporary data record may have, for example, all the features and properties described in relation to the medical image data. For example, the first temporary data record may correspond to the medical image data in terms of dimensionality and/or resolution.

The first correction may include, for example, an autofocus algorithm. For example, the first correction may be configured for the purpose of movement correction (e.g., rigid and/or non-rigid) and/or for the purpose of reducing image artifacts in the medical image data by, for example, filtering (e.g., adaptive filtering). The application of the first correction to the medical image data may improve the image quality of the medical image data. For example, the application of the first correction to the medical image data may increase a signal-to-noise ratio (SNR) of the medical image data and/or reduce an artifact level of the medical image data. The first temporary data record, which is created by applying the first correction to the image data, may have a better image quality than the medical image data (e.g., an increased signal-to-noise ratio and/or a reduced artifact level).

The first correction may be parameterized. For example, the first correction may include the at least one parameter that may be configured to adjust the first correction. For example, by adjusting the at least one parameter of the first correction, it is possible to adjust a threshold value and/or a value range and/or a spatial dimension and/or a degree of freedom of movement to be used when applying the first correction to the medical image data.

The first correction may include an optimization (e.g., an iterative optimization) of a cost function. In this case, when applying the first correction to the medical image data for the purpose of creating the first temporary data record, a cost value of the cost function may be optimized (e.g., minimized).

In act c), a further temporary data record may be created by applying a further correction to the image data. The further correction may correspond to the first correction in this case. An interference term is applied to the at least one parameter of the first correction. The interference term may be one-dimensional and/or multidimensional (e.g., a numerical value and/or a value sequence that may be applied to the at least one parameter of the first correction, such as additively and/or multiplicatively and/or exponentially).

The application of the interference term to the at least one parameter of the first correction makes it possible to change a scope and/or an effect of the first correction.

The at least one further temporary data record, which is created by applying the further correction to the image data, may include a variation relative to the first temporary data record (e.g., with regard to the artifact to be corrected and/or an image quality).

The trained function may be configured, for example, to compare the first temporary data record and the at least one further temporary data record with regard to an image quality. In this case, the trained function may be configured as a binary comparison operator and/or classifier. At least one parameter of the trained function may be based on an image quality metric. For example, the trained function may be provided by an embodiment of the computer-implemented method for the provision of a trained function.

The trained function may be trained by a machine learning method. The trained function may be, for example, a neural network (e.g., a convolutional neural network (CNN) or a network including a convolutional layer and/or an ordinal neural network (ONN)).

The trained function maps input data onto output data. In this context, the output data may also depend, for example, on one or more parameters of the trained function. The one parameter or the plurality of parameters of the trained function may be determined and/or adjusted by training. The determination and/or adjustment of the one parameter or the plurality of parameters of the trained function may be based, for example, on a pair including training input data and associated training output data (e.g., comparison output data), the trained function being applied to the training input data for the purpose of creating training mapping data. For example, the determination and/or adjustment may be based on a comparison of the training mapping data and the training output data (e.g., the comparison output data). A trainable function (e.g., a function with one or more parameters that have not yet been adjusted) is generally also referred to as a trained function.

Further terms for trained function are trained mapping rule, mapping rule with trained parameters, function with trained parameters, algorithm based on artificial intelligence, and machine learning algorithm. One example of a trained function is an artificial neural network, the arc weights of the artificial neural network corresponding to the parameters of the trained function. The term "neural net" may also be used instead of the term "neural network". For example, a trained function may also be a deep neural network (e.g., deep artificial neural network). A further example of a trained function is a "support vector machine," and, for example, other algorithms of machine learning may be used as a trained function.

The trained function may be trained by back propagation, for example. Training mapping data may first be determined by applying the trained function to training input data. A variation between the training mapping data and the training output data (e.g., the comparison output data) may then be calculated by applying an error function to the training mapping data and the training output data (e.g., the comparison output data). It is further possible iteratively to adjust at least one parameter (e.g., a weighting) of the trained function (e.g., the neural network) based on a gradient of the error function in relation to the at least one parameter of the trained function. By this, the variation between the training mapping data and the training output data (e.g., the comparison output data) may be minimized during the training of the trained function.

The trained function (e.g., the neural network) may have an input layer and an output layer. In this case, the input layer may be configured to receive input data. In addition, the output layer may be configured to provide mapping data. In this case, the input layer and/or the output layer may each include a plurality of channels (e.g., neurons).

The input data of the trained function may be based on the first temporary data record and the at least one further temporary data record. For example, the input data may include the first temporary data record and the at least one further temporary data record.

In this case, the image quality metric may include, for example, a regression of a back projection error (e.g., in the case of a movement correction). Further, the image quality metric may be configured to grade the image quality with regard to x-ray beam hardening and/or a signal-to-noise ratio and/or a class of image artifact (e.g., metal artifacts and/or movement artifacts).

The output data of the trained function may include a switch parameter that specifies whether the first temporary data record has a higher image quality compared with the at least one further temporary data record. The switch parameter may include, for example, a Boolean value and/or an ordinal number in this case. Further, it is possible by this comparison to check whether the optimum of the cost function, the optimum being achieved in act b) according to the parameterization (e.g., the current parameterization) with the at least one parameter of the first correction, is a local optimum or a global optimum. If the comparison reveals that the first temporary data record has a lower image quality relative to the at least one further temporary data record, the at least one further temporary data record may be provided as the image data in act b). The acts b) to d) may then be executed again.

If the comparison reveals that the first temporary data record has a higher image quality compared with the at least one further temporary data record, the first temporary data record may be provided as the corrected medical image data.

In this case, the provision of the first temporary data record as the corrected medical image data may include, for example, storage on a computer-readable storage medium and/or display on a presentation unit and/or transfer to a provision unit. For example, a graphical representation of the corrected medical image data may be displayed on the presentation unit.

The embodiment described above allows improved correction of the medical image data. For example, as a result of applying the at least one interference term to the first correction and subsequently applying the trained function to the input data, it is possible to check whether the optimum achieved in the first correction is a local optimum or a global optimum. This allows the image quality of the medical image data to be improved further despite the complexity of the high-dimensional optimization problem of the first correction.

In a further embodiment of the method for the provision of corrected medical image data, the first correction may include a movement correction and/or a metal artifact correction.

The movement correction may be configured to reduce movement artifacts in the medical image data and/or in the first temporary data record. The movement correction may include a transformation (e.g., rigid and/or non-rigid) of the medical image data. In this case, the transformation of the medical image data may include, for example, a translation and/or rotation and/or deformation of the medical image data.

Further, the metal artifact correction may be configured to reduce metal artifacts in the medical image data and/or in the first temporary data record. The metal artifact correction in this case may include, for example, filtering (e.g., adaptive filtering) of the medical image data.

Movement artifacts and/or metal artifacts in the medical image data may be reduced by the embodiment.

In a further embodiment of the method for the provision of corrected medical image data, the first correction may include a movement correction that is based on a movement model. In this case, the movement model may be adjusted to a movement of at least one part of the examination object that is mapped in the image data.

The movement model may be configured to map (e.g., reproduce) a movement of the at least one part of the examination object. The movement is, for example, rigid and/or non-rigid. Further, the movement model may be configured to map periodic and/or non-periodic movements of the at least one part of the examination object. The at least one part of the examination object may include an anatomical region (e.g., an organ and/or tissue and/or a body part of the examination object). For example, the movement model may map a movement trajectory and/or movement amplitude and/or movement speed of the at least one part of the examination object.

The adjustment of the movement model to the movement of the at least one part of the examination object may take place with reference to anatomical and/or geometrical features (e.g., of the at least one part of the examination object) that are mapped in the image data. The anatomical and/or geometrical features in this case may include, for example, a contour and/or a landmark and/or marker structure. The landmark and/or marker structure is, for example, anatomical. The transformation for movement correction of the medical image data may be determined with reference to the movement model.

The movement model may have one or more movement parameters, for example. For example, the movement model may have a movement parameter for each of the degrees of freedom of movement of the at least one part of the examination object. Each of the movement parameters may be considered as a spline. The adjustment of the movement model (e.g., the movement parameters) to the movement of the at least one part of the examination object may include an iterative and/or sequential optimization of nodes of the respective spline (e.g., spline nodes). By this, it is possible to reduce a dimensionality of the high-dimensional optimization problem. Further, the number of spline nodes to be optimized may be increased with increasing iteration. It is possible, using the movement model, for a movement correction of the medical image data to be particularly well adjusted to the movement of the at least one part of the examination object.

In a further embodiment of the method for the provision of corrected medical image data, a plurality of further temporary data records may be created in act c) by applying the further correction to the image data. Further, a plurality of interference terms may be applied to the at least one parameter of the first correction.

The first correction may be parameterized in one dimension or in a plurality of dimensions by the at least one parameter. In this case, the at least one dimension of the parameterization of the first correction may define, for example, a degree of freedom of movement and/or a spatial dimension and/or temporal dimension for a scope and/or effective region of the first correction. Further, the at least one parameter may define an iteration variable for the iterative optimization of the cost function for the at least one dimension of the parameterization of the first correction.

The plurality of interference terms, these being, for example, at least partly varied, for application to the at least one parameter of the first correction, may differ in dimension and/or a numerical value (e.g., an order of magnitude). The plurality of interference terms may be specified such that the at least one parameter of the first correction may be adjusted along at least one dimension (e.g., a plurality of and/or all dimensions) of the parameterization of the first correction.

The application of a plurality of interference terms, these being, for example, at least partly varied, to the at least one parameter of the first correction, and the creation of a plurality of further temporary data records, may allow better checking of the first correction with respect to whether the optimum achieved in the first correction is a local or global optimum.

In a further embodiment of the method for the provision of corrected medical image data, the first correction may include a movement correction. In this case, the movement correction may include a transformation of the image data along at least one spatial degree of freedom of movement. Further, an interference term relating to the degrees of freedom of movement of the transformation may be applied in each case to the at least one parameter of the movement correction. Further, in act c), a further temporary data record may be created in each case for each of the interference terms.

The movement correction may include a transformation (e.g., a rigid and/or non-rigid transformation) of the medical image data. In this case, the transformation may include, for example, a translation and/or rotation and/or deformation of the medical image data (e.g., along at least one spatial degree of freedom of movement).

The movement correction may be parameterized. For example, the movement correction may have at least one parameter by which it is possible to adjust a threshold value and/or a value range and/or a spatial dimension and/or a degree of freedom of movement to be used when applying the movement correction (e.g., the transformation) to the medical image data.

An interference term relating to the degrees of freedom of movement of the transformation may be applied in each case to the at least one parameter of the movement correction. In this case, the further temporary data records created in the act c) may each feature a change relative to the first temporary data record. The change is caused by the respective interference term.

By applying the trained function to the input data in the act d), it is possible to establish whether the first temporary data record has a higher image quality compared with at least one of the further temporary data records. If the result is negative, it may be inferred that the optimum achieved in the act b) with respect to the cost function of the first correction is only a local optimum.

By applying an interference term relating to the degrees of freedom of movement of the transformation to the at least one parameter of the movement correction in each case, it is possible to check, along a plurality of differing dimensions of the high-dimensional optimization problem of the first correction, whether the optimum achieved in the first correction is a local or global optimum.

In a further embodiment of the method for the provision of corrected medical image data, the at least one interference term may describe a stochastic interference.

The at least one interference term may be specified within a predetermined variance as a stochastic interference relating to the at least one parameter of the first correction. In this case, the variance of the stochastic interference may be adjusted, for example, as a function of the respective dimension of the at least one parameter of the first correction.

The embodiment may allow a more robust optimization of the first correction (e.g., relative to local optima) and consequently an improvement of the image quality of the medical image data.

In a further embodiment of the method for the provision of corrected medical image data, the image quality metric may be based on an entropy and/or variance (e.g., of image values of the input data).

The first and/or the at least one further temporary data record may in each case have a plurality of image points (e.g., pixels and/or voxels). In this case, the image points of the temporary data records may each have an image value (e.g., a grayscale value and/or attenuation value and/or intensity value and/or color value).

In this case, the image quality metric may be configured, for example, to grade the image quality of the image data with reference to the entropy and/or variance of the image values of the first and/or the at least one further temporary data record. In this case, the image quality metric may also grade an entropy of a histogram of image values and/or a total variation of the image values of the first temporary data record and/or the at least one further temporary data record.

It is thereby possible to obtain an improved grading of the image quality of the first temporary data record and the at least one further temporary data record using the image quality metric.

In a further embodiment of the method for the provision of corrected medical image data, the first correction may be based on an optimization of the image quality metric or a further image quality metric.

In a first variant, the first correction may be based on an optimization of the image quality metric. The at least one parameter of the trained function is also based on this image quality metric. If the first correction is configured as a deterministic function, the variation between the first temporary data record and the at least one further temporary data record (e.g., with regard to the image quality) may be brought about by the application of the at least one interference term to the at least one parameter of the first correction.

The first variant may allow a consistent grading of the image quality of the first temporary data record and the at least one further temporary data record when optimizing the cost function of the respective correction and when applying the trained function.

In a second variant, the first correction may be based on an optimization of a further image quality metric. The further image quality metric may differ from the image quality metric. This allows a particularly robust and, for example, independent grading of the image quality of the first temporary data record and the at least one further temporary data record when optimizing the cost functions of the respective correction and when applying the trained function.

In a further embodiment of the method for the provision of corrected medical image data, the medical image data may be recorded by a medical imaging device. In this case, the medical imaging device may be configured as a medical x-ray device and/or computed tomography installation (CT) (e.g., an installation for single photon emission computed tomography (SPECT) and/or a magnetic resonance installation (MRT) and/or a positron emission tomography installation (PET) and/or an ultrasound device).

The method may be configured to improve the image quality of medical image data that is recorded using an imaging modality and/or various imaging modalities.

In a further embodiment of the method for the provision of corrected medical image data, the creation of the first temporary data record in act b) may include a reconstruction from the image data. Further, the creation of the at least one further temporary data record in act c) may include a reconstruction from the image data. In act d), if the result is negative, the at least one further temporary data record may be provided as the image data in act b) after application of a back transformation.

The reconstruction may include, for example, an inverse radon transformation and/or a back projection (e.g., a filtered back projection) and/or an inverse Fourier transformation. The first temporary data record may be reconstructed from the image data in act b). Further, the at least one further temporary data record may be reconstructed from the image data in act c). In this case, the first correction and/or the further correction may be applied, for example, before and/or after the respective reconstruction. Further, the first correction and/or the further correction may be applied as part of the reconstruction. For example, the first correction and/or the further correction may be applied to at least one parameter of the respective reconstruction. The first temporary data record and/or the at least one further temporary data record may differ from the image data in at least one image property (e.g., a dimensionality and/or resolution). For example, the image data may be spatially resolved in 2D, and the first temporary data record and/or the at least one further temporary data record may be spatially resolved in 3D. By virtue of the input data of the trained function being based on the first temporary data record and the at least one temporary data record, it is possible in act d) to grade an image quality of the temporary data records reconstructed from the image data after application of the respective correction. If the result is negative, it is possible in act d) to apply a back transformation to the at least one further temporary data record. The back transformation may take the form of an inverse mapping to the reconstruction from the image data.

The embodiment may therefore allow the image quality of the first temporary data record and the at least one further temporary data record to be graded after the respective correction and the reconstruction have been applied to the image data.

In a further embodiment of the method for the provision of corrected medical image data, the image data may in each case include a projection mapping of the examination object along at least partly varied projection directions.

The medical imaging device for recording the medical image data (e.g., the plurality of projection mappings) may have a source and a detector that may be positioned in a defined arrangement. In an embodiment of the medical imaging device as a medical x-ray device (e.g., as a medical C-arm x-ray device) and/or a computed tomography installation, the source may be an x-ray source and the detector may be an x-ray detector.

The at least partly varied projection directions may each describe a path of a beam (e.g., a central and/or middle beam) between the source and the detector (e.g., a central detector point) of the medical imaging device at the time the respective projection mapping is recorded. For example, the projection directions may each describe an angulation (e.g., a rotational travel) of the medical imaging device in relation to the examination object and/or an isocenter.

In this case, the isocenter may describe a spatial point about which the defined arrangement of source and detector may move (e.g., rotate, such as during the recording of the plurality of projection mappings). The at least partly varied projection directions may pass through the isocenter in each case. The isocenter is, for example, shared by the projection directions.

The first temporary data record and/or the at least one further temporary data record may be reconstructed from the projection mappings. In this case, the reconstruction may include an inverse radon transformation and/or a filtered back projection. Further, the back transformation that is executed in act d) if the result is negative may include a radon transformation and/or a virtual projection mapping of the further temporary data record.

The embodiment can enable a reduction in image artifacts (e.g., movement artifacts) that may have been caused during and/or between the recording of the plurality of projection mappings.

In a second aspect, the present embodiments relate to a computer-implemented method for the provision of a trained function. In this case, in a first act t.a), a first training data record is received. In a second act t.b), at least one further training data record is received. Further, in a third act t.c), an image quality parameter is determined in each case by applying an image quality metric to the first training data record and the at least one further training data record. By comparing the image quality parameters, the first training data record or the at least one further training data record is then identified as a comparison data record. The comparison data record has the highest image quality. In a fourth act t.d), the trained function is applied to input data. The input data is based on the first training data record and the at least one further training data record. In this case, by applying the trained function, it is determined whether the first training data record has a higher image quality compared with the at least one further training data record. In a fifth act t.e), at least one parameter of the trained function is adjusted based on a comparison of the comparison data record determined in act t.c) with the result from act t.d). The trained function is then provided in a sixth act t.f).

Further, the acts described above and forming part of the method for the provision of a trained function may be executed to some extent simultaneously and/or consecutively.

The receipt of the first training data record and/or the at least one further training data record may include, for example, capture and/or readout from computer-readable data memory and/or receipt from a data memory unit (e.g., a database).

The first training data record and/or the at least one further training data record may have, for example, all the properties of the first temporary data record and/or the at least one further temporary data record. The properties are described above in relation to the computer-implemented method for the provision of corrected medical image data, and vice versa.

The first training data record and/or the at least one further training data record may also be simulated. Alternatively or additionally, the first training data record and the at least one further training data record may be created by applying the acts a) to c) of a method for the provision of corrected medical image data to medical training image data. In this case, the medical training image data can have, for example, all properties of the medical image data. The properties are described above in relation to the computer-implemented method for the provision of corrected medical image data, and vice versa. For example, the medical training image data may be recorded and/or simulated by a medical imaging device.

In act t.c), it is possible to determine the one image quality parameter in each case by applying the image quality metric to the first training data record and the at least one further training data record. The image quality parameters in this case may each grade an artifact level (e.g., a class of image artifact) and/or a signal-to-noise ratio (SNR) in the first training data record and in the at least one further training data record. The image quality parameters may also have a value in each case (e.g., a normalized value) that grades the image quality of the respective training data record. By comparing the image quality parameters, it is possible to identify the first training data record or the at least one further training data record as a comparison data record. The comparison data record has the highest image quality (e.g., an optimum image quality parameter).

Further, by applying the trained function to the input data in the act t.d), it is possible to determine whether the first training data record has a higher image quality compared with the at least one further training data record. The output data of the trained function may include a switch parameter that specifies whether the first training data record has a higher image quality compared with the at least one further training data record. Depending on the switch parameter, the training data record having the comparatively highest image quality may be provided as a result data record of the trained function.

In act t.e), the at least one parameter of the trained function may be adjusted based on a comparison of the comparison data record determined in act t.c) with the result (e.g., the result data record) from act t.d). The at least one parameter of the trained function may be adjusted in act t.e) such that the first training data record or the at least one further training data record that was identified as the result data record from application of the trained function matches the comparison data record.

The provision of the trained function may include, for example, storage on a computer-readable storage medium and/or transfer to a provision unit.

By virtue of the method, it is possible to provide a trained function that may be used in an embodiment of the computer-implemented method for the provision of corrected medical image data.

In a third aspect, the present embodiments relate to a provision unit that is configured to execute a computer-implemented method for the provision of corrected medical image data.

The provision unit may include a computing unit, a memory unit, and an interface. The provision unit may be configured to execute these methods and aspects thereof, by the interface and the computing unit being configured to execute the corresponding method acts. For example, the interface may be configured to execute the act a) and/or d). Further, the computing unit and/or the memory unit may be configured to execute the acts b) and/or c).

The advantages of the provision unit correspond essentially to the advantages of the computer-implemented method for the provision of corrected medical image data. Features, advantages, or alternative embodiments cited in this context may equally be transferred to the other subject matter and vice versa.

The present embodiments may further relate to a training unit that may be configured to execute the inventive computer-implemented method described above for the provision of a trained function and respective aspects thereof. The training unit may include a training interface, a training memory unit, and a training computing unit. The training unit may be configured to execute these methods and respective aspects thereof, by the training interface, the training memory unit, and the training computing unit being configured to execute the corresponding method acts. For example, the training interface may be configured to execute the acts t.a) and/or t.f). Further, the training computing unit and/or the training memory unit may be configured to execute the acts t.b) to t.e).

The advantages of the training unit correspond essentially to the advantages of the computer-implemented method for the provision of a trained function. Features, advantages, or alternative embodiments cited in this context may equally be transferred to the other subject matter and vice versa.

In a fourth aspect, the present embodiments relate to a medical imaging device having a proposed provision unit. The medical imaging device (e.g., the provision unit) is configured in this case to execute the method for the provision of corrected medical image data. Further, the medical imaging device is configured to record and/or receive and/or provide the medical image data.

The medical imaging device may be configured as, for example, a medical x-ray device (e.g., a medical C-arm x-ray device), and/or a computed tomography installation (CT), and/or a magnetic resonance facility (MRT), and/or a positron emission tomography installation (PET), and/or an ultrasound device. The medical imaging device may include a provision unit that is configured to execute the acts of a method.

The advantages of the medical imaging device correspond essentially to the advantages of the method for the provision of corrected medical image data. Features, advantages, or alternative embodiments cited in this context may equally be transferred to the other subject matter and vice versa.

In a fifth aspect, the present embodiments relate to a computer program product including a computer program that may be loaded directly into a memory of a provision unit, with program sections for executing all acts of the computer-implemented method for the provision of corrected medical image data when the program sections are executed by the provision unit; alternatively or additionally, the computer program may be loaded directly into a training memory of a training unit, with program sections for executing all acts of a method for the provision of a trained function and/or an aspect thereof when the program sections are executed by the training unit.

The present embodiments may further relate to a computer-readable storage medium (e.g., a non-transitory computer-readable storage medium), on which program sections that may be read and executed by a provision unit are stored to execute all acts of the computer-implemented method for the provision of corrected medical image data when the program sections are executed by the provision unit, and/or on which program sections that may be read and executed by a training unit are stored to execute all acts of the method for the provision of a trained function and/or the respective aspects when the program sections are executed by the training unit.

The present embodiments may further relate to a computer program or computer-readable storage medium, including a trained function that is provided by a computer-implemented method of the present embodiments or an aspect thereof.

A largely software-based realization has the advantage that provision units and/or training units that are already in use may also be upgraded easily by a software update in order to work in the inventive manner. In addition to the computer program, such a computer program product may optionally include additional parts such as, for example, documentation and/or additional components, as well as hardware components such as, for example, hardware keys (e.g., dongles, etc.) for using the software.

BRIEF DESCRIPTION OF THE DRAWINGS

The same reference signs are used for same features in different figures, in which.

DETAILED DESCRIPTION

Figure 1:
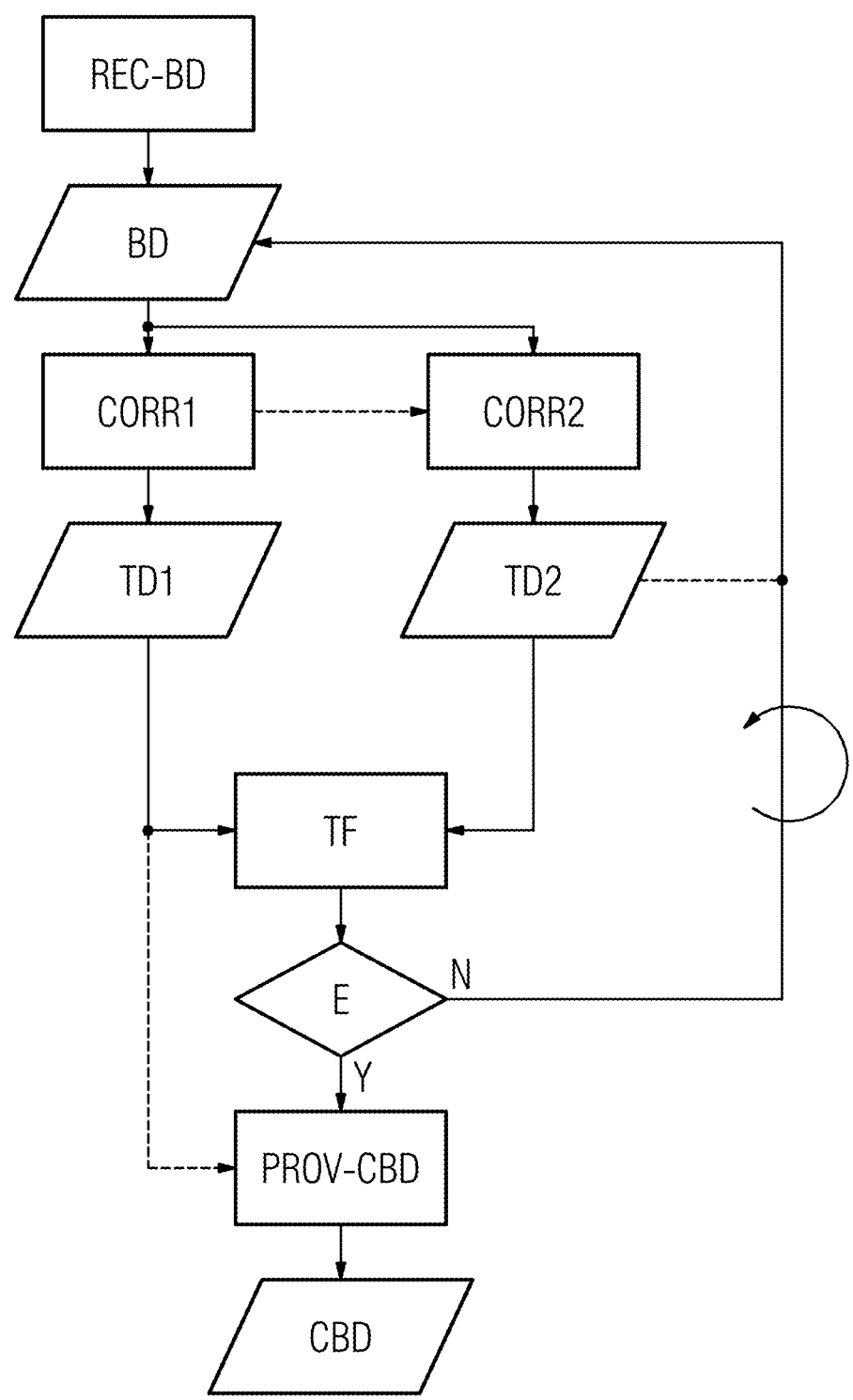
FIGS. 1 and 2 show schematic illustrations of different embodiments of a computer-implemented method for the provision of corrected medical image data.

FIG. 1 shows an embodiment of a computer-implemented method for provision of corrected medical image data PROV-CBD. In a first act a), medical image data BD of an examination object may be received REC-BD. Further, in a second act b), a first temporary data record TD1 may be created by applying a first correction CORR1 to the image data BD. In a third act c), at least one further temporary data record TD2 may be created by applying a further correction CORR2 to the image data BD. In this case, the further correction CORR2 may correspond to the first correction CORR1 with at least one interference term. The at least one interference term is applied to at least one parameter of the first correction CORR1. In this case, the interference term may describe, for example, a stochastic interference. In a fourth act d), a trained function TF may be applied to input data. The input data is based on the first temporary data record TD1 and the at least one further temporary data record TD2. Further, at least one parameter of the trained function TF may be based on an image quality metric. In this case, the image quality metric may be based on an entropy and/or variance of image values of the input data. Further, the first correction CORR1 may be based on an optimization of the image quality metric or a further (e.g., different) image quality metric. By applying the trained function TF, it is possible to establish E whether the first temporary data record TD1 has a higher image quality compared with the at least one further temporary data record TD2. If a result is positive Y, the first temporary data record TD1 may be provided PROV-CBD as the corrected medical image data CBD. If the result is negative N, the at least one further temporary data record TD2 is provided as the image data BD in act b), and the acts b) to d) are executed again.

Further, in act c), a plurality of further temporary data records TD2 may be created by applying the further correction CORR2 to the image data BD, where a plurality of interference terms may be applied to the at least one parameter of the first correction CORR1.

The first correction CORR1 may include a movement correction that may moreover be based on a movement model. In this case, the movement model may be adjusted to a movement of at least one part of the examination object that is mapped in the image data BD. For example, the movement correction may include a transformation of the image data BD along at least one spatial degree of freedom of movement. In this case, an interference term relating to the degrees of freedom of movement of the transformation may be applied in each case to the at least one parameter of the movement correction. In act c), a further temporary data record TD2 may be created in each case for each interference term. Alternatively or additionally, the first correction CORR1 may include a metal artifact correction.

Figure 2:
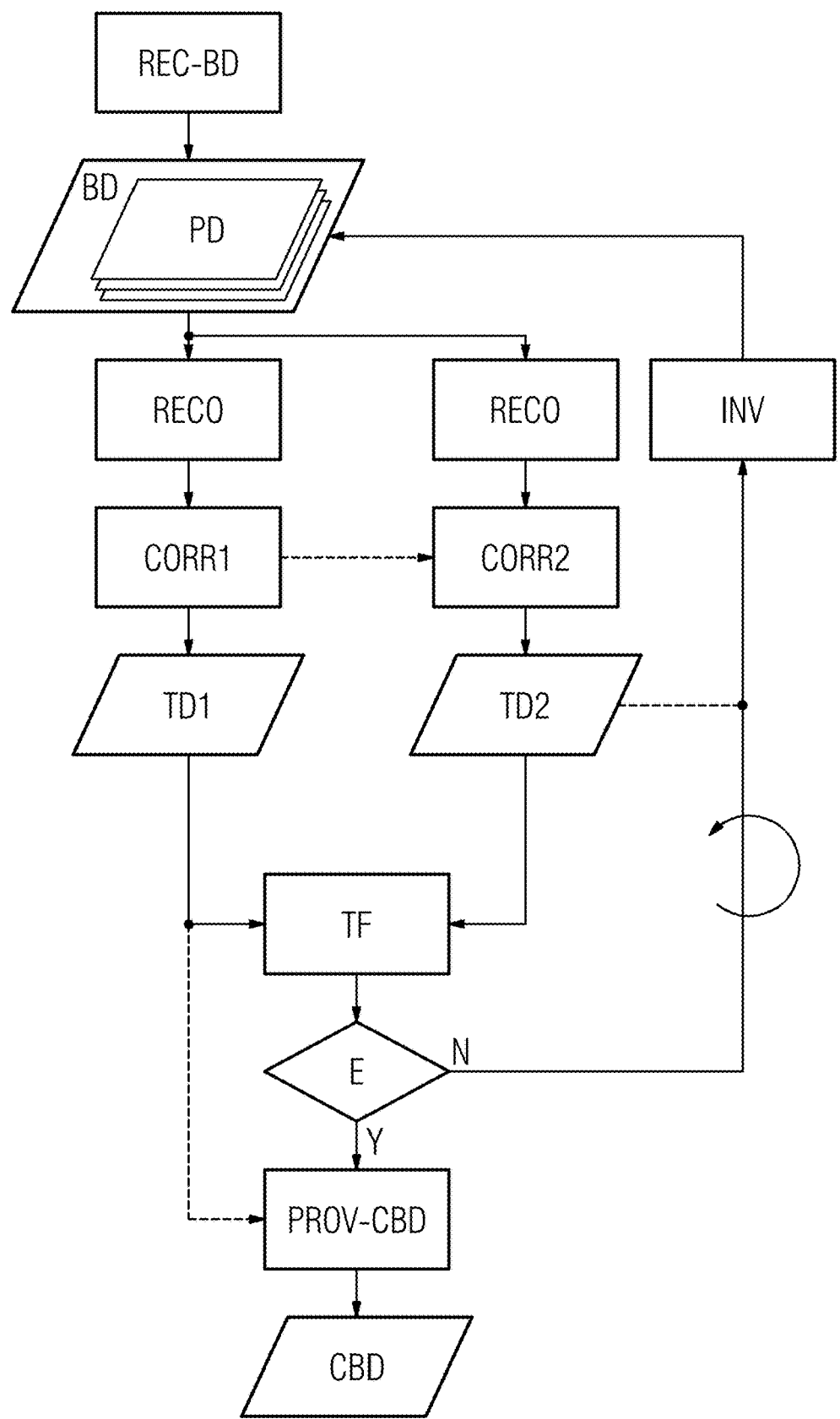

FIG. 2 shows a schematic illustration of a further embodiment of a method for the provision of corrected medical image data PROV-CBD. In this case, the image data BD may include in each case a projection mapping PD of the examination object along at least partly varied projection directions. Further, the creation of the first temporary data record TD1 in act b) may include a reconstruction RECO from the image data BD (e.g., the projection mappings PD). Similarly, the creation of the at least one further temporary data record TD2 may include a reconstruction RECO from the image data BD (e.g., the projection mappings PD). In act d), if the result is negative N, the at least one further temporary data record TD2 may be provided as the image data BD (e.g., the projection mappings PD) in the act b) after application of a back transformation INV.

Figure 3:
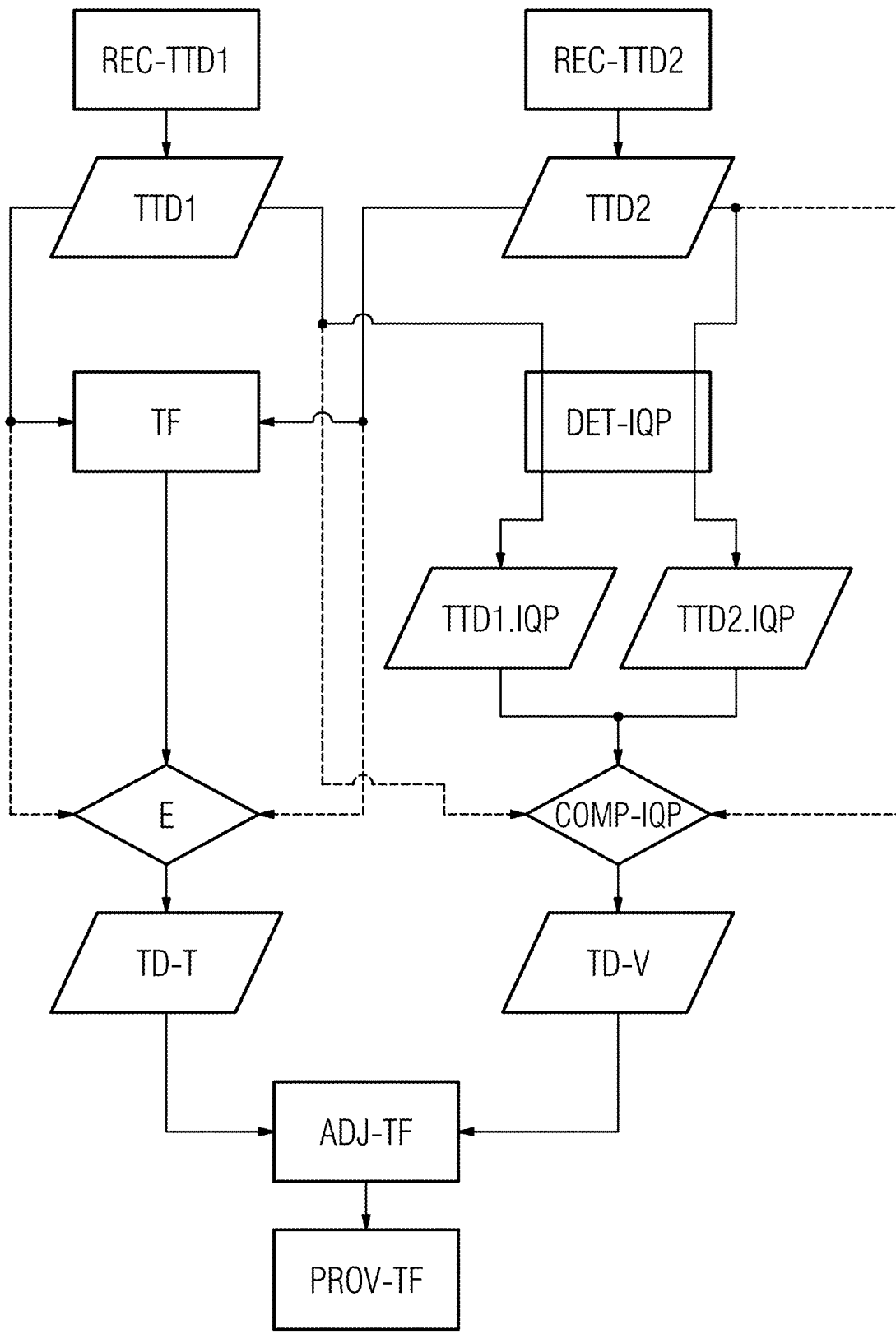
FIG. 3 shows a schematic illustration of one embodiment of a method for the provision of a trained function.

FIG. 3 schematically illustrates one embodiment of a method for the provision of a trained function PROV-TF. In this case, in a first act t.a), a first training data record TTD1 may be received REC-TTD1. In a second act t.b), at least one further training data record TTD2 may be received REC-TTD2. In a third act t.c), an image quality parameter TTD1.IQP and TTD2.IQP may be determined DET-IQP in each case by applying an image quality metric to the first training data record TTD1 and the at least one further training data record TTD2. In this case, by comparing COMP-IQP the image quality parameters TTD1.IQP and TTD2.IQP, the first training data record TTD1 or the at least one further training data record TTD2 may be identified as a comparison data record TD-V. The comparison data record TD-V has the highest image quality. In a fourth act t.d), the trained function TF may be applied to input data. The input data is based on the first training data record TTD1 and the at least one further training data record TTD2. In this case, by applying the trained function TF, it is possible to determine E whether the first training data record TTD1 has a higher image quality compared with the at least one further training data record TTD2. The output data of the trained function TF may include a switch parameter that specifies whether the first training data record TTD1 has a higher image quality compared with the at least one further training data record TTD2. Depending on the switch parameter, the training data record TTD1 or TTD2 having the comparatively higher image quality may be provided as the result data record TD-T of the trained function TF. In a fifth act t.e), at least one parameter of the trained function TF may be adjusted based on a comparison of the comparison data record TD-V determined in act t.c) with the result (e.g., the result data record TD-T) from act t.d). In a sixth act t.f), the trained function TF may be provided PROV-TF.

Figure 4:
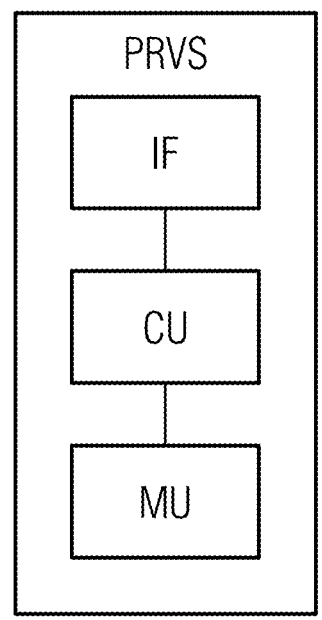
FIG. 4 shows a schematic illustration of one embodiment of a provision unit.

FIG. 4 schematically illustrates one embodiment of a provision unit PRVS. In this case, the provision unit PRVS may include an interface IF, a computing unit CU, and a memory unit MU. The provision unit PRVS may be configured to execute a method for providing corrected image data PROV-CBD and aspects of the method, by the interface IF, the computing unit CU, and the memory unit CU being configured to execute the corresponding method acts. For example, the interface IF may be configured to execute the acts a) and/or d). Further, the computing unit CU and/or the memory unit MU may be configured to execute the acts b) and/or c).

Figure 5:
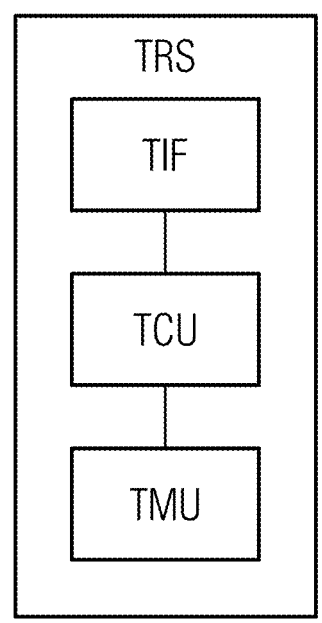
FIG. 5 shows a schematic illustration of one embodiment of a training unit.

FIG. 5 shows a schematic illustration one embodiment of a training unit TRS. The training unit TRS may include a training interface TIF, a training memory unit TMU, and a training computing unit TCU. The training unit TRS may be configured to execute a method for the provision of a trained function PROV-TF and aspects of the method, by the training interface TIF, the training memory unit TMU, and the training computing unit TCU being configured to execute the corresponding method acts. For example, the training interface TIF may be configured to execute the acts t.a), t.b), and/or t.f). Further, the training computing unit TCU and/or the training memory unit TMU may be configured to execute the acts t.c) to t.e).

The provision unit PRVS and/or the training unit TRS may be, for example, a computer, a microcontroller, or an integrated circuit. Alternatively, the provision unit PRVS and/or the training unit TRS may be a computer cluster or a cloud computer. The provision unit PRVS and/or the training unit TRS may also be configured as a virtual system that is executed on a real computer, a cluster, or a cloud (e.g., virtualization).

An interface IF and/or a training interface TIF may be a hardware or software interface (e.g., PCI bus, USB, or Firewire). A computing unit CU and/or a training computing unit TCU may include hardware elements or software elements (e.g., a microprocessor or a field programmable gate array (FPGA)). A memory unit MU and/or a training memory unit TMU may be realized as non-permanent working memory (e.g., random access memory (RAM)) or permanent mass memory (e.g., hard disk, USB stick, SD card, solid state disk).

The interface IF and/or the training interface TIF may include, for example, a plurality of sub-interfaces which execute different acts of the respective methods. In other words, the interface IF and/or the training interface TIF may also be considered as a multiplicity of interfaces IF or a multiplicity of training interfaces TIF, respectively. The computing unit CU and/or the training computing unit TCU may include, for example, a plurality of computing sub-units that execute different acts of the respective method. In other words, the computing unit CU and/or the training computing unit TCU may also be considered as a multiplicity of computing units CU or a multiplicity of training computing units TCU, respectively.

Figure 6:
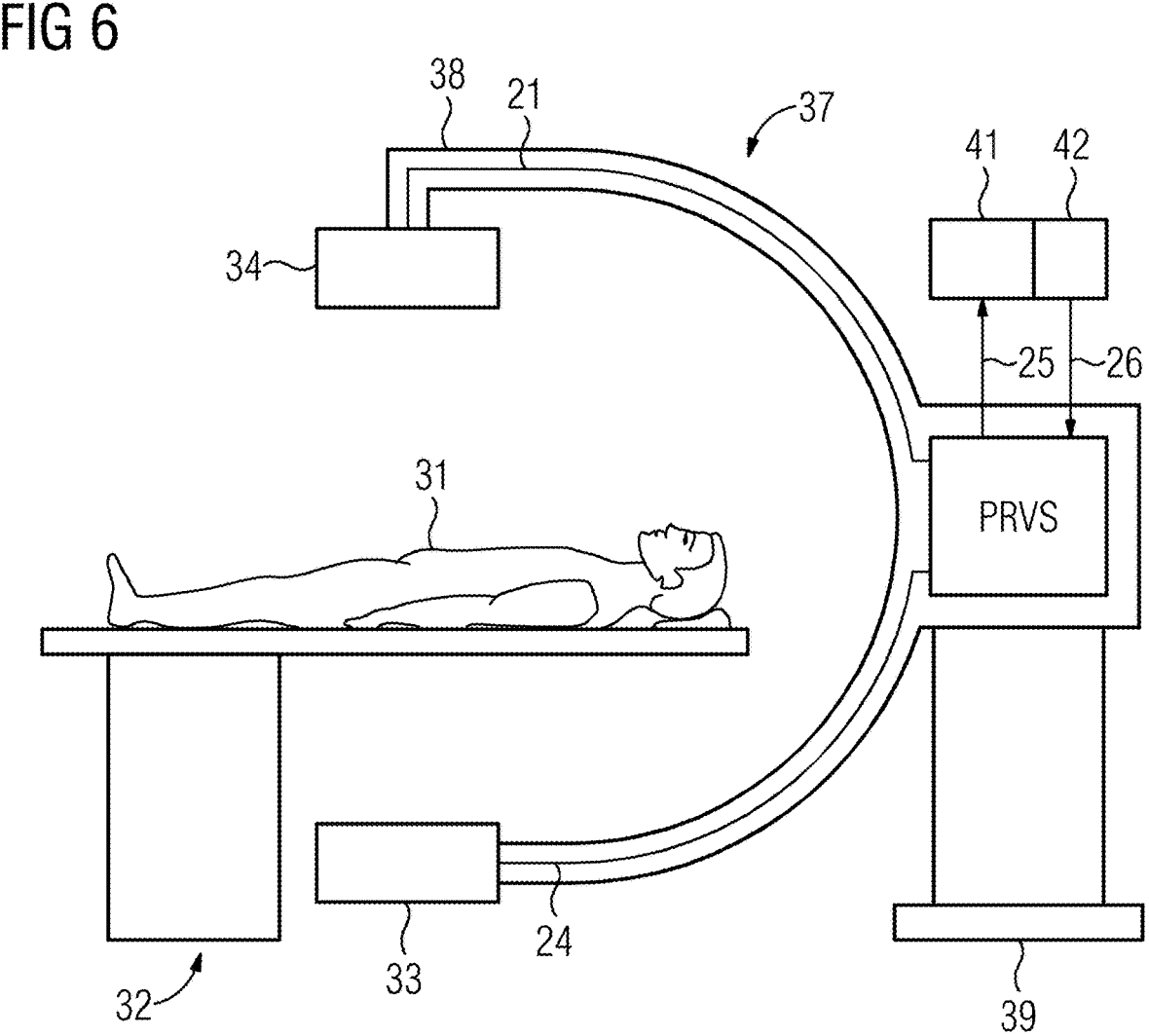
FIG. 6 shows a schematic illustration of one embodiment of a medical C-arm x-ray device as an example of a medical imaging device.

FIG. 6 schematically illustrates a medical C-arm x-ray device 37 as an example of a proposed medical imaging device. In this case, the medical C-arm x-ray device 37 may include a provision unit PRVS. Further, the medical C-arm x-ray device 37 and, for example, the provision unit PRVS may be configured to execute a proposed method for the provision of corrected medical image data PROV-CBD.

The medical C-arm x-ray device 37 includes, for example, a detector 34 (e.g., an x-ray detector) and an x-ray source 33. For the purpose of recording the time-resolved medical image data BD (e.g., the projection mappings PD), an arm 38 of the C-arm x-ray device 37 may be so mounted as to be mobile about one axis or a plurality of axes. The medical C-arm x-ray device 37 may further include a movement device 39 that allows movement of the C-arm x-ray device 37 in the room.

For the purpose of recording the medical image data BD (e.g., the projection mappings PD) of an examination object 31 that is arranged on a patient support facility 32, the provision unit PRVS may send a signal 24 to the x-ray source 33. The x-ray source 33 may thereupon emit a beam of x-rays. When the beam of x-rays strikes a surface of the detector 34 after interacting with the examination object 31, the detector 34 may send a signal 21 to the provision unit PRVS. The provision unit PRVS may receive the medical image data BD (e.g., the projection mappings PD, such as on the basis of the signals 21).

The medical C-arm x-ray device 37 may also include an input unit 42 (e.g., a keyboard) and/or a presentation unit 41 (e.g., a monitor and/or display). The input unit 42 may be integrated in the presentation unit 41 (e.g., in the case of a capacitive and/or resistive input display). In this way, a user input at the input unit 42 allows the medical C-arm x-ray device 37 (e.g., the method for the provision of corrected medical image data PROV-CBD) to be controlled. For this purpose, the input unit 42 may send, for example, a signal 26 to the provision unit PRVS.

Further, the presentation unit 41 may be configured to display information and/or graphical presentations of information from the medical C-arm x-ray device 37 and/or the provision unit PRVS and/or further components. For this purpose, the provision unit PRVS can send, for example, a signal 25 to the presentation unit 41. For example, the presentation unit 41 may be configured to display a graphical presentation of the medical image data BD and/or the corrected medical image data CBD.

The schematic illustrations contained in the figures described above do not indicate any scale or measurement ratio whatsoever.

Both the methods described in detail above and the illustrated apparatuses are merely exemplary embodiments that may be modified in all manner of ways by a person skilled in the art without thereby departing from the scope of the invention. Further, use of the indefinite article "a" or "an" does not preclude multiple instances of the features concerned. Likewise, the terms "unit" and "element" do not preclude the relevant components consisting of a plurality of interacting sub-components, which may also be spatially distributed if applicable.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for provision of corrected medical image data, the computer-implemented method comprising:
   receiving medical image data of an examination object;
   creating a first temporary data record, the creating of the first temporary data record comprising applying a first correction to the medical image data, the applying of the first correction to the medical image data comprising movement correcting the medical image data, reducing image artifacts in the medical image data, or a combination thereof;
   creating at least one further temporary data record, the creating of the at least one further temporary data record comprising applying a further correction to the medical image data, wherein the further correction corresponds to the first correction with at least one interference term that is applied to at least one parameter of the first correction;
   applying a trained function to input data, wherein the input data is based on the first temporary data record and the at least one further temporary data record, wherein at least one parameter of the trained function is based on an image quality metric;
   determining whether the first temporary data record has a higher image quality compared to the at least one further temporary data record based on the applying of the trained function to the input data;
   providing the first temporary data record as the corrected medical image data when a result of the determining is positive, the providing of the first temporary data record as the corrected medical image data comprising storing, by a memory, the corrected medical image data, displaying, by a display, the corrected medical image data, or the storing and the displaying; and
   repeating the creating of the first temporary data record, the creating of the at least one further temporary data record, and the applying of the trained function to the input data using the at least one further temporary data record as the medical image data when the result of the determining is negative.

2. The method of claim 1, wherein the first correction comprises a movement correction, a metal artifact correction, or a combination thereof.

3. The method of claim 2, wherein the first correction comprises a movement correction that is based on a movement model, and
   wherein the movement model is adjusted to at least one part of the examination object that is mapped in the medical image data.

4. The method of claim 1, wherein creating the at least one further temporary data record comprises creating a plurality of further temporary data records, the creating of the plurality of further temporary data records comprising applying the further correction to the medical image data,
   wherein a plurality of interference terms are applied to the at least one parameter of the first correction.

5. The method of claim 4, wherein the first correction comprises a movement correction,
   wherein the movement correction comprises a transformation of the medical image data along at least one spatial degree of freedom of movement, wherein an interference term relating to the degrees of freedom of movement of the transformation is applied in each case to the at least one parameter of the movement correction, wherein creating the at least one further temporary data record comprises creating a further temporary data record in each case for each interference term of the plurality of interference terms.

6. The method of claim 1, wherein the at least one interference term describes a stochastic interference.

7. The method of claim 1, wherein the image quality metric is based on an entropy, variance, or the entropy and the variance of image values of the input data.

8. The method of claim 1, wherein the first correction is based on an optimization of the image quality metric or a further image quality metric.

9. The method of claim 1, wherein the medical image data is recorded by a medical imaging device,
wherein the medical imaging device is configured as a medical x-ray device, a computed tomography installation, a magnetic resonance installation, a positron emission tomography installation, an ultrasound device, or any combination thereof.

10. The method of claim 1, wherein creating the first temporary data record comprises a reconstruction from the medical image data,
wherein creating the at least one further temporary data record comprises a reconstruction from the medical image data,
wherein when the result is negative, the at least one further temporary data record is provided as the image data in the creating of the first temporary data record after application of a back transformation.

11. The method of claim 10, wherein the medical image data includes in each case a projection mapping of the examination object along at least partly varied projection directions.

12. A computer-implemented method for provision of a trained function, the computer-implemented method comprising:
receiving a first training data record;
receiving at least one further training data record;
applying an image quality metric to the first training data record and the at least one further training data record, such that an image quality parameter is determined in each case;
identifying the first training data record or the at least one further training data record as a comparison data record, the identifying of the comparison data record comprising comparing the image quality parameters, the comparison data record having a highest image quality;
applying the trained function to input data, wherein the input data is based on the first training data record and the at least one further training data record;
determining whether the first training data record has a higher image quality compared to the at least one further training data record based on the applying of the trained function;
adjusting at least one parameter of the trained function based on a comparison of the comparison data record with a result of the applying of the trained function to the input data;
providing the trained function, the providing of the trained function comprising storing, by a memory, the trained function;
receiving medical image data of an examination object;
creating a first temporary data record, the creating of the first temporary data record comprising applying a first correction to the medical image data, the applying of the first correction to the medical image data comprising movement correcting the medical image data, reducing image artifacts in the medical image data, or a combination thereof;
creating at least one further temporary data record, the creating of the at least one further temporary data record comprising applying a further correction to the medical image data, wherein the further correction corresponds to the first correction with at least one interference term that is applied to at least one parameter of the first correction; and
applying the trained function to input data, wherein the input data is based on the first temporary data record and the at least one further temporary data record, wherein at least one parameter of the trained function is based on an image quality metric.

13. A provision unit comprising:
a processor configured to provide corrected medical image data, the provision of the corrected medical image data comprising:
receipt of medical image data of an examination object;
creation of a first temporary data record, the creation of the first temporary data record comprising application of a first correction to the medical image data, the application of the first correction to the medical image data comprising movement correction of the medical image data, reduction of image artifacts in the medical image data, or a combination thereof;
creation of at least one further temporary data record, the creation of the at least one further temporary data record comprising application of a further correction to the medical image data, wherein the further correction corresponds to the first correction with at least one interference term that is applied to at least one parameter of the first correction;
application of a trained function to input data, wherein the input data is based on the first temporary data record and the at least one further temporary data record, wherein at least one parameter of the trained function is based on an image quality metric;
determination of whether the first temporary data record has a higher image quality compared to the at least one further temporary data record based on the application of the trained function to the input data;
provision of the first temporary data record as the corrected medical image data when a result of the determining is positive; and
repetition of the creation of the first temporary data record, the creation of the at least one further temporary data record, and the application of the trained function to the input data using the at least one further temporary data record as the medical image data when the result of the determining is negative; and
a display configured to display the corrected medical image data.

14. A medical imaging device comprising:
a provision unit comprising:
a processor configured to provide corrected medical image data, the provision of the corrected medical image data comprising:
receipt of medical image data of an examination object;

creation of a first temporary data record, the creation of the first temporary data record comprising application of a first correction to the medical image data, the application of the first correction to the medical image data comprising movement correction of the medical image data, reduction of image artifacts in the medical image data, or a combination thereof;

creation of at least one further temporary data record, the creation of the at least one further temporary data record comprising application of a further correction to the medical image data, wherein the further correction corresponds to the first correction with at least one interference term that is applied to at least one parameter of the first correction;

application of a trained function to input data, wherein the input data is based on the first temporary data record and the at least one further temporary data record, wherein at least one parameter of the trained function is based on an image quality metric;

determination of whether the first temporary data record has a higher image quality compared to the at least one further temporary data record based on the application of the trained function to the input data;

provision of the first temporary data record as the corrected medical image data when a result of the determining is positive; and repetition of the creation of the first temporary data record, the creation of the at least one further temporary data record, and the application of the trained function to the input data using the at least one further temporary data record as the medical image data when the result of the determining is negative; and a display configured to display the corrected medical image data, wherein the medical imaging device is configured to record the medical image data, receive the medical image data, provide the medical image data, or any combination thereof.

15. In a non-transitory computer-readable storage medium that stores instructions executable by a provision unit of a medical imaging device to provide corrected medical image data, by a training unit to provide a trained function, or by the provision unit to provide the corrected medical image data and the training unit to provide the trained function, the instructions comprising:

providing the corrected medical image data, the providing of the corrected medical image data comprising:

receiving medical image data of an examination object;

creating a first temporary data record, the creating of the first temporary data record comprising applying a first correction to the medical image data, the applying of the first correction to the medical image data comprising movement correcting the medical image data, reducing image artifacts in the medical image data, or a combination thereof;

creating at least one further temporary data record, the creating of the at least one further temporary data record comprising applying a further correction to the medical image data, wherein the further correction corresponds to the first correction with at least one interference term that is applied to at least one parameter of the first correction;

applying a trained function to first input data, wherein the first input data is based on the first temporary data record and the at least one further temporary data record, wherein at least one parameter of the trained function is based on an image quality metric;

determining whether the first temporary data record has a higher image quality compared to the at least one further temporary data record based on the applying of the trained function to the first input data;

providing the first temporary data record as the corrected medical image data when a result of the determining is positive, the providing of the first temporary data record as the corrected medical image data comprising storing, by a memory, the corrected medical image data, displaying, by a display, the corrected medical image data, or the storing and the displaying; and repeating the creating of the first temporary data record, the creating of the at least one further temporary data record, and the applying of the trained function to the first input data using the at least one further temporary data record as the medical image data when the result of the determining is negative;

providing the trained function, the providing of the trained function comprising:

receiving a first training data record;

receiving at least one further training data record;

applying an image quality metric to the first training data record and the at least one further training data record, such that an image quality parameter is determined in each case;

identifying the first training data record or the at least one further training data record as a comparison data record, the identifying of the comparison data record comprising comparing the image quality parameters, the comparison data record having a highest image quality;

applying the trained function to second input data, wherein the second input data is based on the first training data record and the at least one further training data record;

determining whether the first training data record has a higher image quality compared to the at least one further training data record based on the applying of the trained function;

adjusting at least one parameter of the trained function based on a comparison of the comparison data record with a result of the applying of the trained function to the second input data; and providing the trained function; or a combination thereof.

* * * * *